United States Patent [19]

Koslow

[11] Patent Number: 6,015,608
[45] Date of Patent: Jan. 18, 2000

[54] LIQUID ABSORBENT PAD WITH ANTI-GEL-BLOCK LAMINATE

[75] Inventor: Evan E. Koslow, Weston, Conn.

[73] Assignee: Koslow Technologies Corporation, Orange, Conn.

[21] Appl. No.: 09/090,011

[22] Filed: Jun. 3, 1998

[51] Int. Cl.[7] .................................................. A61F 13/15
[52] U.S. Cl. ..................... 428/304.4; 604/382; 604/380; 156/73.1; 156/73.5
[58] Field of Search ................... 604/382, 380; 156/73.1, 73.5, 327; 428/304.4

[56] References Cited

U.S. PATENT DOCUMENTS

| | | |
|---|---|---|
| 4,592,751 | 6/1986 | Gegelys ............................... 604/382 X |
| 5,601,542 | 2/1997 | Melius et al. . |
| 5,643,237 | 7/1997 | Fechillas et al. .................... 604/382 X |
| 5,713,881 | 2/1998 | Rezai et al. .......................... 604/382 X |
| 5,792,513 | 8/1998 | Koslow et al. .......................... 427/195 |

*Primary Examiner*—Daniel Zirker
*Attorney, Agent, or Firm*—Ohlandt, Greeley, Ruggiero & Perle, L.L.P.

[57] ABSTRACT

A liquid absorbent pad has incorporated therein a plurality of liquid-absorbent laminated segments. The segments include super-absorbent particles. The segments are separated from one another and liquid dams between them prevent water-swollen particles from migrating throughout the pad. The dams may be formed by welding, adhesives, or by other means.

17 Claims, 1 Drawing Sheet

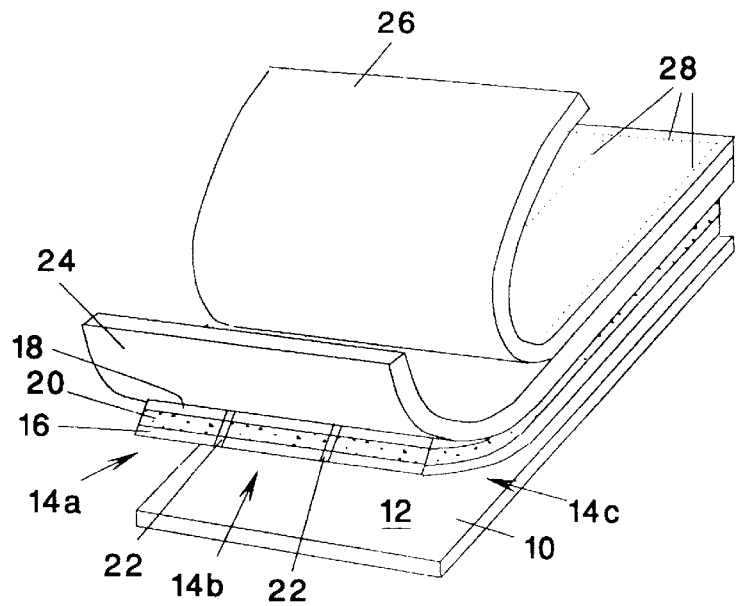
FIG. 1
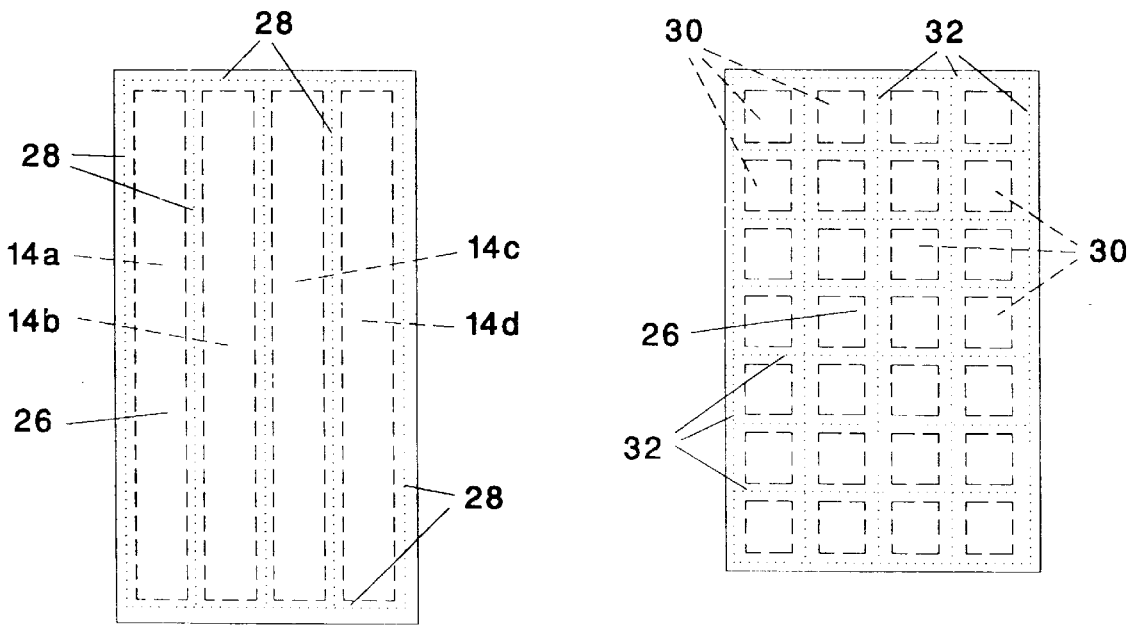
FIG. 2
FIG. 3

LIQUID ABSORBENT PAD WITH ANTI-GEL-BLOCK LAMINATE

BACKGROUND OF THE INVENTION

1. Technical Field

This invention pertains to the manufacture of absorbent products. Such products may be used, for example, in diapers and feminine hygiene products.

2. Description of the Prior Art

A conventional product for use, for example, as a diaper may include a liquid impermeable backsheet, a layer of fluff pulp, an acquisition layer which may be, for example an air laid polypropylene medium, and possibly a spun-bonded polypropylene or nylon layer to be placed next to the skin. Included within the fluff pulp layer may be particles of a super-absorbent material such as, for example, a super-absorbent acrylic-based polymer obtained from Stockhausen Corporation, Greensboro, N.C. These super-absorbent particles absorb water and swell markedly. Upon swelling, the particles tend to interlock with one another, thereby forming a gel. This gel inhibits the passage and absorption of additional liquid.

In order to overcome the gelling problem, it has been proposed to incorporate into the material a laminate containing particles of non-gelling super-absorbent polymers. An example of such a laminate will be found in co-pending U.S. patent application Ser. No. 08/813055 now U.S. Pat. No. 5,792,513, filed Mar. 7, 1997 by Evan E. Koslow et al. for CONTINUOUS SOLID STATE WEB COATING PROCESS. That application is incorporated herein by reference. The disclosure of the referenced application describes the coating of a thin substrate web, such as tissue paper, with an admixture of super-absorbent polymer particles and much smaller particles of a thermoplastic binder. This mixture is applied to the substrate web by the application of pressure and heat sufficient to soften the binder particles. The binder particles are hydrophobic and thereby prevent the water-swollen super-absorbent particles from coalescing into a gel. Also available for such purposes are particles of super-absorbent polymers having cross-linked surfaces which tend to be anti-gel-blocking. A preferred form of the coated web described in the reference application comprises two tissue layers which form a sandwich with the absorbent and binder particles therebetween.

Laminated absorbent pads have been prepared utilizing the customary liquid-impermeable back sheet, but substituting the above-mentioned non-gelling laminate for the fluff pulp layer. An acquisition layer for the laminate comprises an air laid medium having copious large capillaries. Finally, a spun-bonded material may be employed as a skin contact layer. Tests have revealed that such a produce employing a non-gelling laminate will absorb water 30–50% faster than a commercial product employing a fluff pulp core. However, there still remains one problem. While it is advantageous that the super-absorbent particles do not coalesce into a gel, they do create a problem because of their tendency to migrate within the diaper or other product once wetted. In a wet diaper worn by an active toddler, the vastly swollen water-containing particles will not stay in one position but will instead migrate throughout the diaper pad. Accordingly, it is a primary object of the present invention to provide an improved liquid-absorbent pad employing liquid-absorbing laminates wherein migration of the liquid-swollen particles is eliminated or substantially reduced. Other objects, features, and advantages will become apparent from the following description and appended claims.

SUMMARY OF THE INVENTION

The invention comprises forming a liquid absorbent laminate as set forth in the referenced co-pending application. The laminate sheet is cut or isolated into segments. The segments are positioned on the liquid-impermeable backing material and are spaced or isolated from one another. A liquid acquisition layer is then positioned over the laminate segments and, if desired, a liquid-permeable skin-contacting layer is positioned on the acquisition layer. Thereafter, the layered composite is bonded into a unitary pad. Means are provided between the laminate segments for preventing the transfer of liquid-absorbent particles between adjacent laminate segments.

BRIEF DESCRIPTION OF DRAWINGS

FIG. 1 is a greatly enlarged perspective view of a portion of a pad constructed in accordance with the present invention, partially separated to reveal its internal construction;

FIG. 2 is a plan view of one form of a pad constructed in accordance with the present invention; and FIG. 3 is a view similar to FIG. 2, illustrating a modification of the present invention.

BEST MODE FOR CARRYING OUT THE INVENTION

The structure illustrated in FIG. 1 comprises an outer layer 10 of a liquid impervious material, such as a thin plastic film or hydrophobic membrane, having an outer surface (not shown) and an inner surface 12. Mounted on the inner surface 12 of the outer layer 10 are a plurality of laminate segments, such as strips 14a–c. These strips are cut from a laminated sheet as described in the above-referenced co-pending patent application. Accordingly, the strips are substantially identical in construction. Each includes a bottom layer 16 of tissue, an upper layer 18 of tissue, and an intermediate layer 20 of super-absorbent polymer particles bonded to the bottom and upper tissue layers by thermoplastic binder particles. The laminate strips 14a–c are separated from one another by spaces 22. Mounted on the laminate strips is a liquid acquisition layer 24. The acquisition layer 24 may be of any material currently used for this purpose and known to those skilled in the art. It may be, for example, an air laid medium including fibers forming a copious number of relatively large capillaries. Completing the structure of FIG. 1 is an optional liquid-permeable skin-contacting spun-bonded medium 26.

The layers comprising the structure of FIG. 1 are bonded to one another by means such as an ultrasonic weld 28. The weld 28 extends about the periphery of or through each of the laminate strips 14, traversing the intermediate spaces 22. FIG. 2 shows a portion of the pad of FIG. 1 comprising four laminate strips 14a–d and illustrates the manner in which the weld 28 surrounds and encapsulates each of the laminate strips. In effect, the weld 28 forms liquid-impervious dams which prevent migration of the water-swollen particles between the strips or between segments of the laminated medium. Migration along the length of each strip is restricted by inter-particulate friction within the strip and migration toward the skin is restricted by the close packed fibers of the acquisition layer 24 and also by the skin contact film 26, if employed.

FIG. 3 illustrates a slight modification of the invention illustrated in FIGS. 1 and 2. This modification differs in that, rather than strips 14 of laminate, smaller segments, such as squares 30 are employed. Otherwise, the construction is essentially the same and the squares 30 are isolated from one another by means of the dam formed by the weld 32.

It is believed that the many advantages of this invention will now be apparent to those skilled in the art. It will also be apparent that a number of variations and modifications may be made therein without departing from its spirit and scope. For example, in place of welding, the dams may be formed using adhesives or other similar joining techniques. Accordingly, the foregoing description is to be construed as illustrative only, rather than limiting. This invention is limited only by the scope of the following claims.

I claim:

1. A liquid absorbent pad which comprises:
   an outer layer of a substantially liquid-impervious material having an outer surface and an inner surface;
   a plurality of liquid-absorbent laminate segments positioned on the inner surface of said liquid impervious material and spaced from one another, each of said laminate segments comprising a liquid permeable first substrate web having a first surface upon which is deposited a particulate, substantially non-gelling, liquid absorbent and particles of a thermoplastic binder fused to both of said particulate liquid absorbent and said first surface;
   a liquid-permeable acquisition layer positioned over said plurality of laminate segments; and
   liquid-impervious means bonding the outer layer and liquid acquisition layers together with the plurality of liquid-absorbent laminate segments therebetween, the liquid impervious bonding means disposed for preventing transfer of liquid-absorbent particles between adjacent laminate segments.

2. The pad of claim 1 wherein said liquid transfer preventing means comprises a dam within the space separating adjacent laminate segments.

3. The pad of claim 2 wherein said dam substantially encloses each of said laminate segments.

4. The pad of claim 1 further comprising a liquid permeable layer positioned over said acquisition layer.

5. The pad of claim 1 wherein each of said laminate segments comprises, in addition, a second substrate web having a second surface spaced from said first surface and fused to said thermoplastic binder.

6. The pad of claim 5 further comprising a liquid permeable layer positioned over said acquisition layer.

7. The pad of claim 6 wherein said liquid transfer preventing means comprises a dam within the space separating adjacent laminate segments.

8. The pad of claim 7 wherein said dam substantially encloses each of said laminate segments.

9. The pad of claim 8, further comprising a liquid permeable layer positioned over said acquisition layer.

10. The method of making a liquid absorbent pad which comprises:
    providing an outer layer of a substantially liquid-impervious material having an outer surface and an inner surface;
    positioning on the inner surface of said outer layer, a plurality of liquid-absorbent laminate segments, said segments being spaced or isolated from one another, each of said laminate segments comprising a liquid permeable first substrate web having a first surface upon which is deposited a particulate, substantially non-gelling, liquid absorbent and particles of a thermoplastic binder fused to both of said particulate liquid absorbent and said first surface;
    positioning a liquid-permeable acquisition layer over said plurality of laminate segments; and
    sealing said outer layer to said acquisition layer by liquid-impervious means suitable for substantially preventing transfer of liquid-absorbent particles between adjacent laminate segments.

11. The method of claim 10 wherein the sealing step comprises welding.

12. The method of claim 11 wherein the sealing step comprises ultrasonic welding.

13. The method of claim 10 wherein the sealing step comprises adhesive application.

14. The method of claim 10 comprising, in addition, the step of positioning a liquid permeable layer over said acquisition layer prior to said sealing step.

15. The method of claim 14 wherein the sealing step comprises welding.

16. The method of claim 15 wherein the sealing step comprises ultrasonic welding.

17. The method of claim 14 wherein the sealing step comprises adhesive application.

* * * * *